(12) United States Patent
Hall et al.

(10) Patent No.: US 8,027,739 B2
(45) Date of Patent: Sep. 27, 2011

(54) MEDICAL DEVICE HAVING A GLASS COATING AND METHOD THEREFOR

(75) Inventors: Peter Hall, Andover, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 737 days.

(21) Appl. No.: 11/855,088

(22) Filed: Sep. 13, 2007

(65) Prior Publication Data
US 2009/0076576 A1    Mar. 19, 2009

(51) Int. Cl.
*A61N 1/05*    (2006.01)

(52) U.S. Cl. .......... 607/121; 607/37; 607/115; 607/116

(58) Field of Classification Search .................. 607/121, 607/37, 115, 116; 216/67; 427/2.24
See application file for complete search history.

(56) References Cited

U.S. PATENT DOCUMENTS

| | | | | |
|---|---|---|---|---|
| 4,841,101 A | * | 6/1989 | Pollock | 174/152 GM |
| 2007/0179554 A1 | * | 8/2007 | Iyer et al. | 607/37 |

* cited by examiner

*Primary Examiner* — Carl H Layno
*Assistant Examiner* — Pamela M Bays
(74) *Attorney, Agent, or Firm* — Faegre & Benson LLP

(57) ABSTRACT

A medical device having at least one glass coating between a first and second component. The glass coating forms a portion of a strong, hydrothermally stable joint between components or provides insulation, or tailors an impedance and/or capacitance of an electrode.

10 Claims, 3 Drawing Sheets

MEDICAL DEVICE HAVING A GLASS COATING AND METHOD THEREFOR

TECHNICAL FIELD

This relates to the field of medical devices, and more specifically to a medical device having a glass coating.

TECHNICAL BACKGROUND

Medical devices, such as implantable leads and pulse generators, include components that are joined together, for example, with adhesive. However, adhesives typically degrade in wet or hot environments, and joints made with adhesives also can degrade in such an environment.

SUMMARY

The inventors have discovered a hydrothermally stable joint for use in medical devices. A medical device includes a first component and a second component, and a joint therebetween. The first component includes at least one of a metal or a ceramic portion that forms at least a portion of the joint, and at least one of the metal portion or the ceramic portion has a coating of glass thereon, where the coating a glass forms a portion of the joint. The second component includes, in an option, a polymer component. Bonding material such as adhesive is optionally disposed on the coating of glass to form a portion of the joint between the first component and the second component.

In another option, a medical device includes a first component and a second component and a joint formed therebetween. The first component has a coating of glass thereon, where the coating of glass has a substantially similar coefficient of expansion as the coefficient of expansion of the first component. The second component includes a polymer portion that forms at least a portion of the joint.

A method for forming a medical device is further provided herein. The method includes coating at least one of a first component or a second component with a coating of glass, applying energy to the coating of glass and flowing the glass, and disposing the first component directly adjacent to the second component and coupling the first component with the second component. In an option, coupling the first component with the second component includes bonding the first component with the second component, for instance, with medical adhesive.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
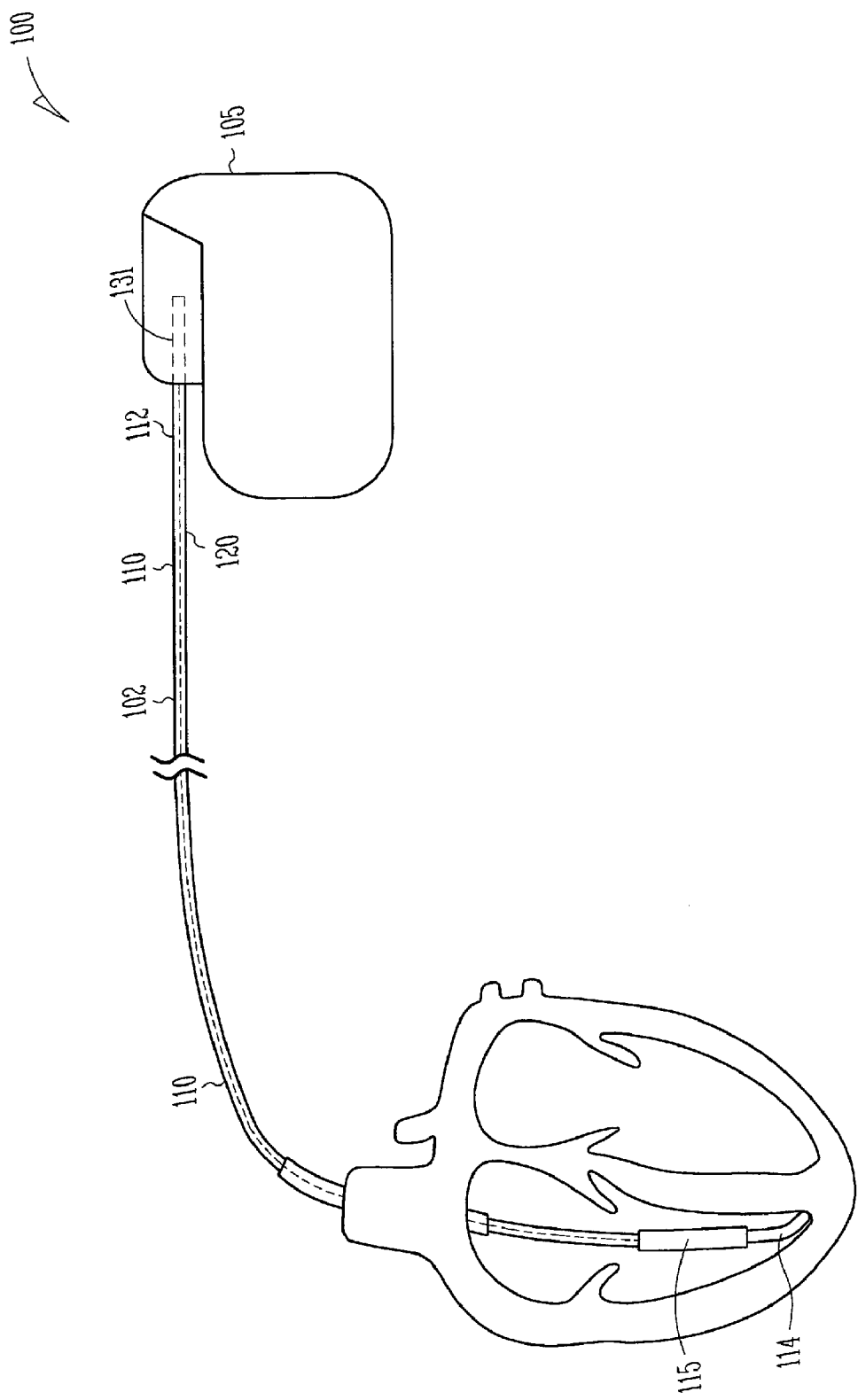
FIG. 1 illustrates a medical device in accordance with at least one embodiment.

An implantable device 100, such as a lead 102 for use with an electrical stimulator 105, is illustrated in FIG. 1. The implantable device 100 includes a lead body 110, and at least one elongate conductor 120 contained within the lead body 110. The lead body 110 extends from a proximal end 112 to a distal end 114. The proximal end 112 of the lead is electrically coupled with the electrical stimulator 105, for example, with a terminal pin 131.

The electrical stimulator 105 generically represents, but is not limited to, cardiac function management (referred to as "CFM") systems such as pacers, cardioverters/defibrillators, pacers/defibrillators, biventricular or other multi-site resynchronization or coordination devices such as cardiac resynchronization therapy (referred to as "CRT") devices, sensing instruments, drug delivery systems, neurostimulation devices, or organ stimulation devices.

The electrical stimulator 105 includes a source of power as well as an electronic circuitry portion. In one example, the electronic circuitry includes microprocessors to provide processing, evaluation, and to determine and deliver electrical shocks or pulses of different energy levels and timing for neurostimulators or ventricular defibrillation, cardioversion, or pacing of heart in response to sensed cardiac arrhythmia including fibrillation, cardiac resynchronization, tachycardia, or bradycardia. In another example, the electrical stimulator 105 is a battery-powered device that senses intrinsic signals of the heart and generates a series of timed electrical discharges.

The implantable device 100 further includes, in one option, one or more electrodes 115. The one or more electrodes 115 are each electrically coupled with the at least one conductor 120. The electrode 115 allows for electrical signals to be delivered to the tissue from the electrical stimulator 105. The implantable device 100 further includes, in one option, features to allow the lead body to be fixated within a patient. For example, in one option, the lead body includes passive fixation features, such as one or more tines. In another option, the lead body includes an active fixation assembly, such as a fixation helix.

The implantable medical devices include components that further include a joint, coupling a first component with a second component to form another component, for example. Examples of components that can be coupled together include, but are not limited to, an electrode, a terminal, a lead body, a distal fixation component, a metal component, a polyurethane component, or a silicone rubber component.

Figure 2:
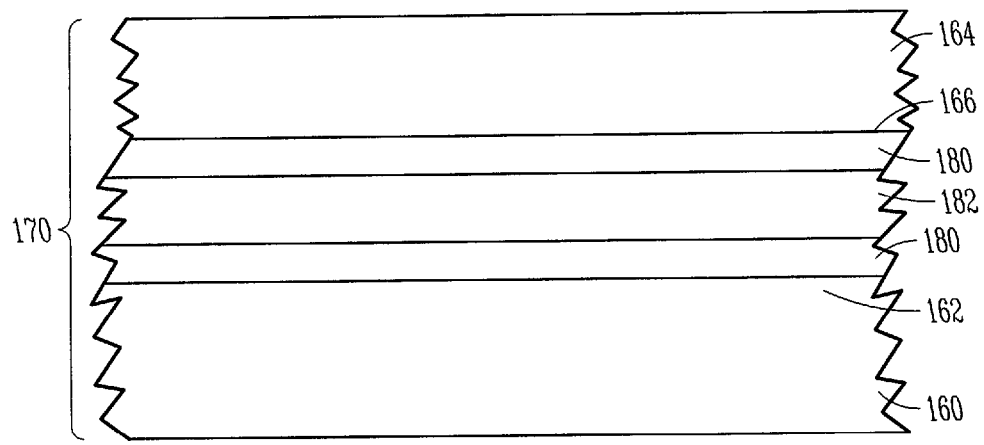
FIG. 2 illustrates a joint of a medical device in accordance with at least one embodiment.

Referring to FIG. 2, a portion of a medical device including a joint is shown. A first component 160 of a first portion 162, and a second component 164 having a second portion 166 are shown, where the first and second components 160, 164 are part of a medical device. The first component 160 and the second component 164 are brought together and are coupled together to form a joint 170 of the medical device.

The first component 160 includes, in an option, a coating 180 of glass thereon, which assists in forming a portion of the joint 170. In a further option, bonding material 182 is disposed on the coating of glass and further forms a portion of the joint 170. If the second component 164 is formed of a metal or ceramic, the second component 164 can optionally include a coating of glass, in addition to or in alternative to the first component 160. The first portion 162 including the coating 180 of glass, in an option, is bonded with the second portion 166 with a bonding material, and forms the joint 170.

Figure 5:
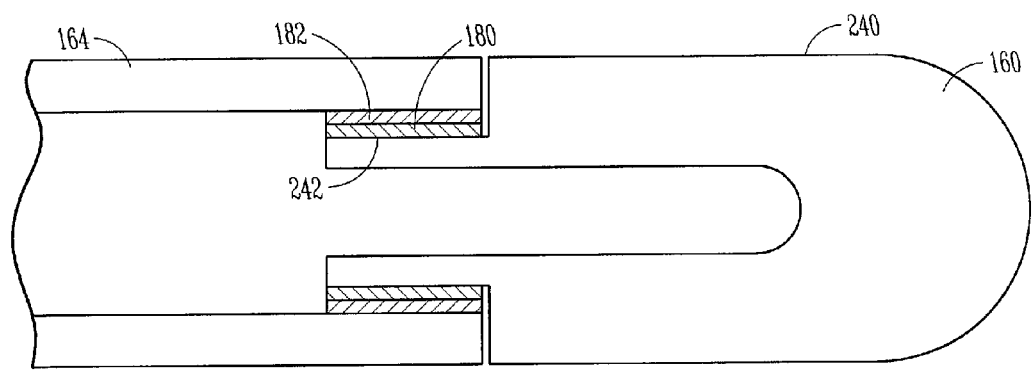
FIG. 5 illustrates a cross-sectional view of a portion of a medical device in accordance with at least one embodiment.

In an option, the first component includes a metal component, and the second component includes a polymer component. In a further option, the first component 160 is at least a partially metal component, including, but not limited to titanium, stainless steel, MP35N, platinum, platinum/iridium alloy, tantalum niobium, or combinations or alloys thereof. In another option, the first component 160 includes a coating of metallic material. Example components of the first component include, but are not limited to, a terminal including a terminal pin 131 (FIG. 1), a ring electrode 210 (FIG. 3) of an implantable lead (FIG. 1), an electrode (FIG. 5). In another option, the first component 160 is at least a partially ceramic component, or can be entirely formed of ceramic. In an option, the second component 164 is a polymer component, including, but not limited to silicone rubber, silicone rubber tubing, polyurethane, ETFE, PTFE, ePTFE, or molded polymer parts.

The glass coating 180 includes, but is not limited to, a soda-lime composition, or a borosilicate composition, either of which, in an option, are non-leaded. The glass coating 180 adheres to the first or second components, such as a metal component, via a reaction between the glass and the surface oxide of the metal that is driven by the high solubility of metal ions in glass. The glass coating 180, in a further option, has substantially similar thermal expansion, such as the coefficient of thermal expansion, as the material of the first or second components 160, 164, such as a metal portion or the ceramic portion of the first component. In an option, the coefficients of thermal expansion are the same. In another option, the coefficients of thermal expansion are within 5% of one another. In another option, the coefficients of thermal expansion are within 10% of one another. In another option, the coefficients of thermal expansion are within 12% of one another. In another option, the coefficients of thermal expansion are within 15% of one another. In another option, the coefficients of thermal expansion are within 20% of one another. In yet another option, the coating of glass has a thickness of about 0.010 inches or less. The glass coating 180 can by hydrated, resulting in a high density of silanol (Si—OH) groups on a surface of the glass coating 180.

In a further option, a bonding material 182, such as adhesive, is disposed between the first and second components, or between the glass coating and the second component prior to bonding the components together. Other materials include, but are not limited to, an adhesive such as acetoxy cure silicone RTV (room temperature vulcanizing) adhesive, silicone adhesives such as oxime cure, alkoxy cure, UV cure, heat cure, pressure sensitivity, epoxy, polyurethane adhesive, or UV cure adhesive. In an option, the bonding material, such as medical adhesive silicone RTV adhesive, includes silanol groups, and forms Si—O—Si strong covalent bonds with the glass coating. In another option, a primer or silane coupling agents can be utilized on the glass coating for added adhesion or water durability. The primer can be used with or without surface treatment of the components.

Figure 3:
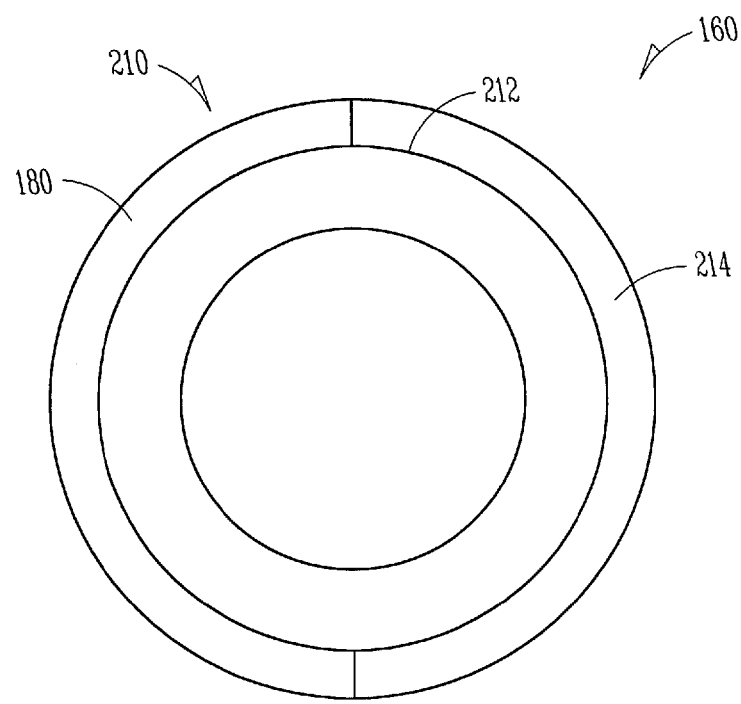
FIG. 3 illustrates a cross-section of an electrode of a medical device in accordance with at least one embodiment.

Referring to FIG. 3, a ring electrode 210 of an implantable lead is an example of a first component 160 having a coating 180 of glass. In an option, the coating 180 of glass is disposed on an outer portion of the ring electrode 210, for instance, along a portion of the outer diameter 212. In another option, the coating 180 of glass can be placed along an inner diameter of the electrode 210, or another surface. The coating 180 forms at least a portion of a joint where it is coupled with other portions of an implantable lead, such as a cardiac lead.

In another option, the coating 180 can be used to tailor the impedance and capacitance of an electrode surface. The electrode 210 can be selectively coated with the glass, by selectively removing the glass coating or selectively depositing the glass coating such that only a portion of the electrode 210 is coated. In an option, the glass coating is applied for instance over a mask, so that only portions of the metal or ceramic electrode are coated. Alternatively, portions of the glass coating can be selectively removed from the electrode, for instance, using one or more of, but not limited to, laser ablation, focused ion beam, or grit blasting. In yet another option, a metal oxide (i.e. IrOx) can be placed on the metal component, glass is applied, and then ablated. The glass can also be selectively placed using a mask to apply the glass. In a further option, a coating other than glass can be placed on the component such as the ring electrode 210. For instance, an IrOx coating 214 can be placed on a portion of the outer diameter 212 of the electrode 210, and the coating 180 of glass can be placed on the outer diameter 212 of the electrode 210. In an option, the IrOx coating 214 covers a half of the outer diameter 212, and the coating 180 of glass covers the other half of the outer diameter 212. In another option, the glass can be coating on at least a portion of the metal oxide coating, such as the IrOx coating.

In another option, the glass coating 180 can be selectively applied to the electrode to allow for pacing only on a myocardial side of an electrode, and/or to avoid extra cardiac pacing, for instance about a half of the outer circumference can be coated, as shown in FIG. 3. In a further option, the glass coating 180 can be patterned on the component, such as the electrode. In an example, the glass coating 180 can be patterned on the component by selective application, such as with a mask, or by selective removal, such as with laser ablation. Energy is applied, such as the glass coating of the electrode is heated, allowing for flowing of the glass. Optionally, the glass coating is treated after the energy is applied, using the optional treatments discussed herein, including, but not limited to hydrating the glass coating. This method allows for the electrode to be selectively insulated with the glass coating.

Figure 4:
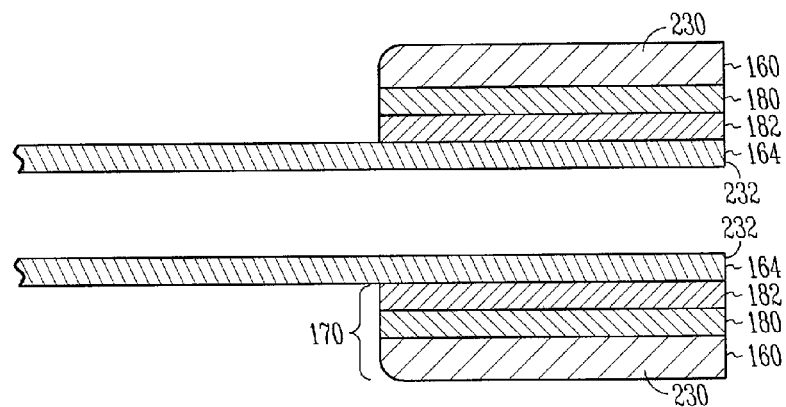
FIG. 4 illustrates a cross-sectional view of a portion of a medical device in accordance with at least one embodiment.

FIG. 4 illustrates a cross-sectional view of a portion of a medical device, such as an implantable cardiac lead, including a first component 160 and a second component 164 brought together to form a joint 170. A robust, hydrothermally stable joint can be formed between the first component 160 and the second component 164. In an option the first component 160 is a metal tube 230, and the second component 164 is a polymer, such as silicone rubber tubing 232. A coating 180 of glass is disposed on an inner surface 236 of the metal tube 230, and an optional bonding material 182 is disposed on an inner portion of the coating 180 of glass. The silicone rubber tubing 232 is bonded to the inner portion of the coating 180 of glass, allowing for the stable joint 170. This joint assembly can be used, for example, for a cardiac lead or a pulse generator header. The coating 180 of glass can be placed alternatively, or in addition to, on the outer surface of the metal tube, and the silicone tubing can be bonded to the outer portion of the coating 180 of glass.

FIG. 5 illustrates a cross-section view of a portion of a medical device, such as an implantable cardiac lead, including a first component 160 and a second component 164 that form a joint. In an example, a first component 160 is an electrode, such as a tip electrode 240 includes a coupling portion 242. The coupling portion 242 has a coating of glass 180 thereon. The electrode, in an option, is a titanium electrode or a Pt/Ir electrode with an optional metal oxide coating 249, such as an IrOx coating. The electrode is fired in an oven to melt and fuse the glass to the metal surface, and/or to the IrOx coating, after the unfused glass coating is applied, for example, by spray coating. A bonding material 182 such as silicone RTV is placed on the glass coating 180, and a second component 164, such as silicone rubber tubing, is placed over the adhesive, and allowed to cure, for example, at room temperature.

A method for making a medical device is further described herein. A first component and/or a second component is coated with a coating of glass. The coating of glass can be applied, in an option, by dip coating, spray coating or sputter coating glass or silicon dioxide, spin coating, coating with a glass frit, coating with a glass powder, or a combination thereof. In an option, the glass frit is placed into a carrier solution, such as water, alcohol, or acetone, and a thin layer is sprayed on to the component. The coating of glass can also include a pre-cursor, such as, but not limited to, a sol gel coating or sol gel material. In a further option, the component to be coated can be masked prior to the coating of glass so that selected portions of the component will be coated with the glass.

Energy is applied to the glass coating, and forms the glass coating, for example by flowing the glass. For example, energy is applied by firing the glass coating with heat in a furnace, or using a sol-gel process, such as drying. Other options for applying energy include, but are not limited to, applying infra red energy, white light, lasers, etc. The glass forms and bonds with the component surface, such as the metal surface or a coated surface, such as a coating of metal oxide on the surface. In an option, the firing temperatures are about 500-1000 degrees C.

In a further option, the glass coating is treated before or after applying energy to the glass. For example, the coating is hydrated or plasma treated. In another option, the glass coating is at least partially etched. In yet another option, a primer is applied to the glass coating prior to or after treating the glass coating. In a further option, the glass coating is applied using a sol-gel material and subsequent drying and/or firing, for example using a sol-gel process. A primer can be used to allow the adhesive to bond better.

The joint is formed by coupling the glass coated component with another component, for example, by bonding. In an option, the other component also is glass coated. In a further option, bonding material, such as medical adhesive, is disposed between the glass coating and the other component which forms the joint. The components are brought together so that a first component is directly adjacent to a second component, coupling the first component with the second component. In an option, the joint is formed, for example, by bonding the components together, in an option, with medical adhesive.

In another example, the method includes dip or spray coating a metal component with a glass frit and isopropyl alcohol or water solvent mixture, letting the solvent evaporate, putting the glass coated metal or ceramic component in a furnace and firing the glass coating so that it bonds to the metal or the ceramic. The glass coated metal is bonded to a polymer, such as a polymer tube, using a bonding material such as, but not limited to silicone RTV adhesive.

The joint for the medical device can be used in an implantable device or component that has adhesive joints exposed to blood or body fluids. Examples include, but not limited to, implantable pacemakers, bonding polymer headers to metal cans, implantable cardioverter defibrillators, electrostimulation devices and medical leads associated with these devices. The joints are stable in wet environments and improve long term performance of the devices.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A medical electrical lead comprising:
   a lead body extending from a proximal end to a distal end, the lead body comprising an elongate conductor contained within the lead body;
   a joint comprising a first component coupled to a second component, wherein one of the first component and the second component is the lead body, the first component including at least one of a metal or a ceramic portion forming at least a portion of the joint, at least one of the metal portion or the ceramic portion including a coating of glass disposed thereon, the coating of glass also forming at least a portion of the joint; and
   adhesive disposed on the coating of glass between the coating of glass and the second component.

2. The medical device as recited in claim 1, wherein the metal portion is a PtIr alloy.

3. The medical device as recited in claim 1, wherein the metal portion includes at least one of a stainless steel, platinum, MP35N, titanium alloy, tantalum, miobium, metal oxide coating, metal nitride coating, or combinations thereof.

4. The medical device as recited in claim 1, wherein the glass coating has a substantially similar thermal expansion as the metal or the ceramic.

5. The medical device as recited in claim 1, wherein the first component is an electrode of an implantable lead.

6. The medical device as recited in claim 1, wherein the first component is a metal component and the second component is a polymer component.

7. A medical electrical lead comprising:
   a lead body extending from a proximal end to a distal end, the lead body comprising an elongate conductor extending within the lead body;
   a joint comprising a first component having a coefficient of expansion coupled to a second component,
      wherein one of the first component and the second component is the lead body, the first component including a coating of glass disposed thereon, the coating of glass forming a portion of the joint and having a substantially similar coefficient of expansion as the coefficient of expansion of the first component and wherein the second component includes a polymer portion that forms at least a portion of the joint; and
      adhesive disposed over the coating of glass between the coating of glass and the second component.

8. The medical device as recited in claim 7, wherein the first component is a metal component.

9. The medical device as recited in claim 8, wherein the metal component is a titanium component.

10. The medical device as recited in claim 7, wherein the first component is a ceramic component.

* * * * *